(12) United States Patent
Taralp

(10) Patent No.: US 8,541,610 B2
(45) Date of Patent: Sep. 24, 2013

(54) PREPARATION OF SUBSTANTIALLY QUATERNIZED AMMONIUM ORGANOSILANE COMPOSITION AND SELF-STABILIZING AQUEOUS SOLUTION THEREOF

(76) Inventor: Alpay Taralp, Istanbul (TR)

( * ) Notice: Subject to any disclaimer, the term of this patent is extended or adjusted under 35 U.S.C. 154(b) by 0 days.

(21) Appl. No.: 13/504,130

(22) PCT Filed: Apr. 21, 2010

(86) PCT No.: PCT/IB2010/051747
§ 371 (c)(1),
(2), (4) Date: Apr. 26, 2012

(87) PCT Pub. No.: WO2011/132020
PCT Pub. Date: Oct. 27, 2011

(65) Prior Publication Data
US 2013/0030207 A1    Jan. 31, 2013

(51) Int. Cl.
*C07F 7/04*    (2006.01)
(52) U.S. Cl.
USPC ............................................ 556/413
(58) Field of Classification Search
USPC ........................................... 556/413
See application file for complete search history.

(56) References Cited

U.S. PATENT DOCUMENTS 6,376,696 B1 *   4/2002   Raab et al. .................... 556/423

FOREIGN PATENT DOCUMENTS

WO     WO 2005099689 A1 * 10/2005

OTHER PUBLICATIONS

Gulengul Duman et al, Modified cotton bearing potential antimicrobial and blood-clotting activity, Abstracts of Papers, 225th ACS National Meeting, New Orleans, LA, United States, Mar. 23-27, 2003, CELL-070.*

* cited by examiner

*Primary Examiner* — Johann R Richter
*Assistant Examiner* — Kofi Adzamli
(74) *Attorney, Agent, or Firm* — Bayramoglu Law Offices, LLC

(57) ABSTRACT

This invention relates to the preparation of a partially quaternized ammonium organosilane composition, and a self-stabilizing aqueous solution of said composition, which serves to yield an antimicrobial polysilsesquioxane coating upon thermal curing. By way of this invention, an aqueous solution is prepared, comprised in part by a partially quaternized ammonium organosilane hydrolysate, characterized in that no further manipulation or addition of potentially costly ingredients are required to yield a stable and hence marketable product.

12 Claims, No Drawings

PREPARATION OF SUBSTANTIALLY QUATERNIZED AMMONIUM ORGANOSILANE COMPOSITION AND SELF-STABILIZING AQUEOUS SOLUTION THEREOF

FIELD OF THE INVENTION

This invention relates to the formation of a partially quaternized organosilane composition from a two-component composition of the starting materials; the preparation of a stable aqueous solution comprising of the inert and hydrolysable reconstituted components of said composition; and the thermal curing of said aqueous solution onto surfaces, yielding an antimicrobial coating.

PRIOR ART

Quaternary ammonium organosilanes (also classified as organosilyl quaternary amines) of the type $CH_3(CH_2)_{11-17}(CH_3)_2N^+(CH_2)_3Si(OR)_3A^-$ are typically formed by quaternizing the corresponding tertiary amine with an appropriate 3-chloropropyl organosilane reagent (Rxn-1). The same quaternized structure has also been constructed via an alternative, parallel synthetic pathway, using the corresponding alkylchloride to quaternized 3-dimethylaminopropyl organosilane (Rxn-1'). Herein, the term "quaternizing" refers to the act of alkylating a tertiary amine functional group. Such synthetic reactions have been achieved in a molten state (i.e., neat) or in the presence of a solvent. In turn, said organosilanes of the general form $CH_3(CH_2)_{11-17}(CH_3)_2N^+(CH_2)_3Si(OR)_3A^-$ may be hydrolyzed to the corresponding organosilantriol, i.e., $CH_3(CH_2)_{11-17}(CH_3)_2N^+(CH_2)_3Si(OR)_3A^-$, and will yield, upon thermal processing, antimicrobial condensation products of the general form $CH_3(CH_2)_{11-17}(CH_3)_2N^+(CH_2)_3Si(OT)_{3-n}(OH)_nA^-$, where $(CH_2)_{11-17}$ denotes an aliphatic saturated chain spanning 11-17 carbon units, R denotes methyl or ethyl, $A^-$ denotes a leaving group, often a halide and most often chloride, n denotes an integer value of 0-2 (and more likely of 0-1), and T denotes a bonded partner comprised of one or more organosilane units and likely an assembly comprised of higher-order oligo- and polysilsesquioxane associations, as well as a substrate bearing hydroxyl groups or an intertwineable surface suitable for bonding.

As documented in the prior art, elevated temperatures and prolonged reaction times are implemented in efforts to promote maximum quaternization over the course of reaction. Aqueous solutions of the ensuing quaternized product are subsequently prepared by direct dilution/dissolution of the material. For this purpose, the material is typically added to a vigorously stirred aqueous solution.

The preparation of said quaternary organosilanes and their subsequent dissolution in water appears trivial; as implied by the illustrations herein, two simple parallel processes, i.e., Rxn-1 & Rxn-2, as well as Rxn-1' & Rxn-2, lead to the same aqueous product. Imparting long-term storage stability, however, to the newly formed aqueous quaternary amine solution, defines a major concern that directly impacts the use and marketability of such antimicrobial formulations. Experience has shown that moderately high aqueous concentrations (e.g. 2-5 wt %) are unstable, leading to the premature sedimentation of polysilsesquioxane-type polymers. To improve shelf-life and storage stability, thus yielding a marketable formulation, several strategies have been implemented following quaternization. Some of the common approaches utilized in order to extend storage life have been to introduce surfactant additives, to coordinate the free silanol ends with stabilizers such as simple sugars and multiple hydroxyl group molecules, to coordinate/associate said quaternary organosilane hydrolysates with hydrophilic polymers, to incorporate non-aqueous solvents such as the toxic methanol, to use alternative aqueous-organic systems, and to apply combinations thereof. In some cases, pH adjustments have been invoked to maximize the benefits imparted by a stabilizer. Thus far, the implementation of such post-quaternization strategies has proved instrumental and necessary to yield marketable water-based formulations. Accordingly, these elaborate formulations, typically sold as aqueous 5 wt % concentrates of the quaternized product, require extra processing and additives, which transmit additional costs to the end user.

U.S. Pat. No. 6,376,696 and WO00/78770 outline a process to prepare a quaternary ammonium silane from tetradecyldimethylamine and 3-chloropropyltrimethoxysilane, in which the yield during quaternization is quantitative and the product is dissolved and stabilized in an aqueous solution containing methyltriglycol as active stabilizer.

U.S. Pat. No. 3,560,385 outlines to a process to prepare a quaternary ammonium silane from octadecyldimethylamine and 3-chloropropyltrimethoxysilane in methyl cellosolve. The yield of quaternization is near quantitative and said product is easily dissolved and retained in water by virtue of methyl cellosolve, acting as active stabilizer.

U.S. Pat. No. 6,613,755 outlines a process to dissolve methanolic solutions of quaternary amines in water, giving an overall concentration below 1 wt % with respect to the final water-methanol solution.

U.S. Pat. No. 6,632,805 and WO97/41729 relate to a process to prepare a quaternary ammonium silane from octadecyldimethylamine and 3-chloropropyltrimethoxysilane. In following a process, which implements pH control and the addition of an active stabilizer, a stable solution of the trioxasilylbicycloctyl intermediate species is obtained. Stabilizers included pentaerythritol, tris(hydroxymethyl)ethane, tris(hydroxymethyl)methane, and similar compounds.

US2005008613 relates to providing a series of novel solid phase carriers coated with a quaternary ammonium organosilane. This document emphasizes the surface application of a quaternary ammonium organosilane solution as opposed to the promotion of solution-phase solubility and long-term stability. This work is also technically distinguishable in that solid-phase carriers are used to support the surface-bonded quaternary ammonium organosilane coating. Carriers form no part of the invention.

JP2091008 relates to obtaining an antimicrobial, water-soluble powder, comprising of a colloidal suspension formed by a combination of a quaternary ammonium organosilane hydrolysate, a perspiration suppressant salt, starch, clay and saccharoses.

US20080181862 relates to the preparation of an antimicrobial polysiloxane. As part of this embodiment, a dimethylaminopropyl organosilane is quaternized using an alkylhalide and the ensuing product is solvated in methanol but not water.

US2010/0028462 relates to the preparation of a water-stable quaternary ammonium organosilane hydrolysate. Here, the key to retaining stability is the incorporation of a non-ionic surfactant.

Exemplifying the full scope of the prior art, Rxn-1 & Rxn-2, as well as Rxn-1' and Rxn-2 collectively depict the process of quaternizing, hydrolyzing and solubilizing (with stabilizers) the organosilane, yielding a stable aqueous solution of the corresponding quaternary ammonium organosilyl hydrolysate. Of the two parallel synthetic pathways, the former (i.e., Rxn-1 & Rxn-2) defines the more predominant industrial process.

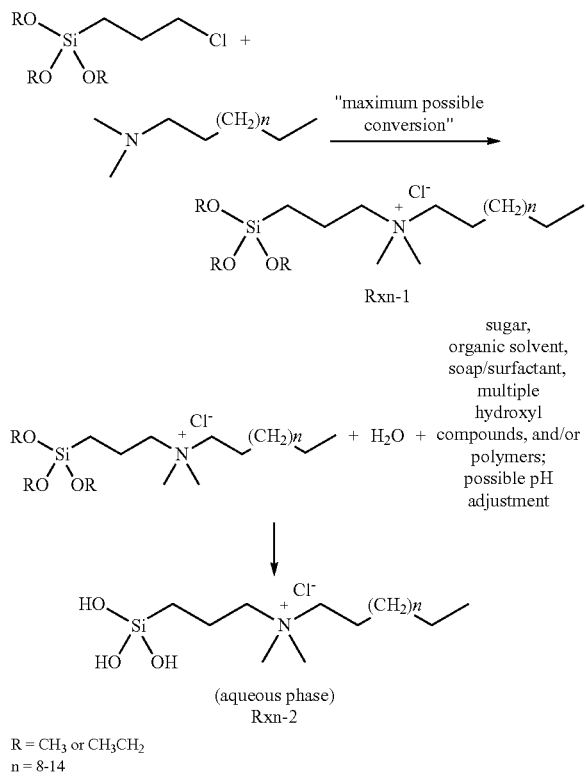

Rxn-1

Rxn-2

R = CH₃ or CH₃CH₂
n = 8-14

To maximize the transformation of tertiary amines and organosilane reagents into the corresponding antimicrobial quaternary ammonium organosilane (Rxn-1), temperatures in excess of 100° C. are typically employed. In practice, the typical maximum attainable conversions have been reported on the order of 90-95% with respect to the limiting reagent (Rxn-1). As rapid precipitation has defined the major problem during aqueous re-constitution of such products, prior efforts to improve aqueous-phase stability have reported the use of one or more of many potential stabilizing additives. Stated more comprehensively, these stabilizers may be classified as sugars, soaps/surfactants, water-compatible co-solvents, silanol group chelators and hydrophilic polymers (Rxn-2). In some cases, pH adjustments have been necessary as a precondition to optimizing the benefits of said stabilizers. In the case of Rxn-1', an alkylhalide is made to react with 3-dimethylaminopropyltrimethoxysilane, affording the same quaternary organosilane product. This time, however, the conversion of starting materials into product may be pushed to near completion at slightly lower reaction temperatures, such as 90° C., apparently due to the higher reactivity of the system in question.

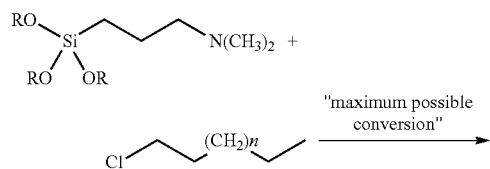

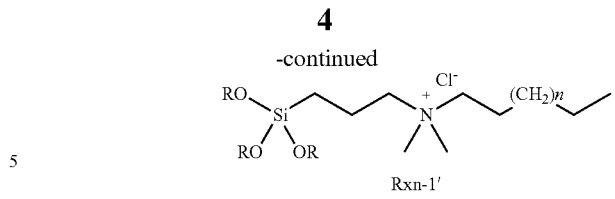

Rxn-1'

R = CH₃
n = 0-11

BRIEF DESCRIPTION OF INVENTION

This invention defines a method to prepare an antimicrobial, partially quaternized ammonium organosilane composition, whose components, when fully dissolved in water, display self-stabilization and long storage-life. Herein, the term "partially" is used to denote the significantly less-than-quantitative formation of the quaternized ammonium organosilane product during the alkylation reactions (Rxn-2-1 and Rxn-2-1'). The term "self-stabilizing" relates to the interaction between water and the products of the quaternization reaction, and the fact that the components of these products collectively afford a stable aqueous solution, which bypasses any further manipulation or need of potentially costly ingredients in order to yield a marketable aqueous concentrate.

Another objective of this invention is to outline a method to resolve the instability and short shelf-life problem of the aqueous quaternary ammonium organosilane hydrolysates. The approach expressed herein is to exploit the seemingly unrelated concept of cutting short the quaternization reaction, which bestows stability to the water-reconstituted components of the composition.

Another objective of this invention is to define a cost-effective and technically facile method to prepare a stable aqueous solution containing quaternized ammonium organosilane hydrolysates.

Another objective of this invention is to define a method to prepare a stable aqueous solution containing quaternized ammonium organosilane hydrolysates, without resorting to established stabilization strategies based on the use of simple sugars, surfactants, multiple hydroxyl-containing molecules, and hydrophilic polymers as mandatory additives.

DETAILED DESCRIPTION OF INVENTION

This invention relates to the preparation of a neat composition comprised of quaternized ammonium organosilanes, i.e., $CH_3(CH_a)_{11-17}(CH_3)_2N^+(CH_2)_{1-6}Si(OR)_3X^-$, and unspent starting materials, which upon dissolution in water yields a stable aqueous solution, containing organosilane hydrolysates (i.e., organosilantriol solutes) primarily of the type $CH_3(CH_a)_{11-17}(CH_3)_2N^+(CH_2)_{1-6}Si(OH)_3X^-$. These organosilane hydrolysates, in turn, form an antimicrobial quaternary coating, i.e., $CH_3(CH_a)_{11-17}(CH_3)_2N^+(CH_2)_{1-6}Si(OT)_{3-n}(OH)_n X^-$, upon thermal curing to a suitable substrate. Here, "a" is 2 or 1 but generally denotes the former, signifying the methylene unit ($—CH_2—$). Still, this notation imparts the flexibility to occasionally replace one or more adjacent pairs of methylene units (i.e., $—CH_2—CH_2—$) in the saturated chain by two methine units (i.e., $—CH=CH—$); accordingly, $(CH_a)_{11-17}$ denotes an aliphatic saturated or unsaturated chain spanning 11-17 carbon units. The carbon chain $(CH_2)_{1-6}$ refers to a length of 1-6 carbon atoms, Z denotes an alkyl unit of 1-4 carbon units, X⁻ denotes a leaving group, often a halide and most often chloride, but also groups such as sulfate, sulfonate, phosphate and phosphonate, n denotes an integer value of 0-2 (and more likely of 0-1), and T denotes a bonded partner comprised of one or more organosilane units and likely an assembly comprised of higher-order oligo- and polysilsesquioxane associations, as well as a substrate bearing hydroxyl groups or an intertwineable surface suitable for bonding. Two features distinguish this invention from the prior art. One feature is the formation of a stable aqueous solution, comprised of (1) the hydrolysis products of the organosilyl quaternary amine component, i.e., $CH_3(CH_a)_{11-17}(CH_3)_2N^+(CH_2)_{1-6}Si(OH)_3X^-$; (2) the hydrated and (where applicable) hydrolyzed starting materials of said organosilyl quaternary amine, also present in substantial amounts in the composition; and (3) potentially any hydrated and (where applicable) hydrolyzed minor by-products of the quaternization reaction, which may arise during heating. The second feature of the invention, a related trait, is the ability to form a stable aqueous solution using this partially quaternized ammonium organosilane composition without resorting to the addition of stabilizers, elaborate formulations, or otherwise manipulating the re-constituted aqueous solution. Hence, the composition itself is self-stabilizing in water.

Just like the quaternary ammonium organosilanes noted in the prior art, the partially-quaternized ammonium organosilane composition of this invention is typically formed by quaternizing the corresponding tertiary amine with an appropriate 3-chloropropyl organosilane reagent, or any alkyl organosilane reagent, bearing a suitable leaving group, X, at the terminus of the alkyl chain (Rxn-2-1). Similarly, the invention also describes the quaternization of the corresponding alkylating agent and an appropriate dimethylamino alkyl organosilane (Rxn-2-1'). The quaternization reaction may be realized in the molten state or with the aid of a solvent, but the former reaction medium is preferred and forms the focus of the invention. Among the components, the antimicrobial activity of this composition is related to that fraction of the composition, which bears the quaternary ammonium organosilane structural component, i.e., $CH_3(CH_a)_{11-17}(CH_3)_2N^+(CH_2)_{1-6}Si(OZ)_3X^-$. Once the partially quaternized composition is reconstituted in water, the quaternized component is hydrolyzed, forming $CH_3(CH_a)_{11-17}(CH_3)_2N^+(CH_2)_{1-6}Si(OH)_3X^-$. Reconstituted aqueous solutions may be applied along most substrates bearing surface hydroxyl groups. Alternatively, said solutions may be perfused into permeable or porous media. During the subsequent thermal processing stage, the organosilyl hydrolysates will crosslink, yielding polysilsesquioxane condensation products along the substrate and (where applicable) within the substrate. The antimicrobial component in particular, may be described as $CH_3(CH_a)_{11-17}(CH_3)_2N^+(CH_2)_{1-6}Si(OT)_{3-n}(OH)_nX^-$.

The innovative aspect of the invention is related to a previously conducted series of in-house investigations, whereof certain features of the prior art were re-evaluated. In forcing the quaternization reaction, long-chain alkyl quaternary amines of the form $CH_3(CH_a)_{11-17}(CH_3)_2N^+(CH_2)_{1-6}Si(OZ)_3X^-$ were synthesized in near-quantitative yield. With such a high product conversion realized, waxy solids were obtained. These solids proved dispersible under aqueous conditions. In accord with the prior art, however, the aqueous-phase stability of these compounds proved unsatisfactory; in particular, sedimentation of silsesquioxane species was noted within a short period. In an effort to better understand the onset of sedimentation, a series of quaternization reactions were deliberately cut short, i.e., heating was terminated before the syntheses had run to completion. Moreover, the termination point of each trial in this series was varied such that the resultant composition of each trial reflected a different product conversion. While those trials substantially approaching maximum quaternization still afforded unstable solutions, trials featuring product conversions of about 52-57% in particular afforded a viscous neat material that was noted to readily dissolve in water at concentrations of up to 12.5 wt %, affording stable solutions particularly at concentrations at or below 10 wt %. Still lower product conversions (i.e., yields <52% on the basis of the limiting reagent) also formed stable aqueous solutions. However, the lower limit of self-stabilization was not assessed in view that only the quaternary component would be antimicrobial and therefore commercially interesting. What could be claimed was that this composition—comprised of the target quaternary amine, a substantial portion of unused starting materials, and potential minor byproducts thereof—had dissolved into water, forming an aqueous solution at room temperature, which displayed a much better aqueous-phase storage stability than what might have been anticipated on the basis of the information available in the prior art. Accordingly, the distinguishing step or feature of this invention was readily definable in that a stable formulation had been obtained, without resorting to the use of additives or further chemical manipulations. Such findings only applied at product conversions not significantly exceeding 57% yield on the basis of the limiting reagent. In our experience, a product conversion that yielded 45-65% of the quaternary ammonium component gave acceptable results, with the optimum range being 52-57%. Tests indicated that %5 wt aqueous stocks had retained their solubility, surface applicability, post-cure bond fastness and antimicrobial activity even after being allowed to age for 24-30 weeks at room temperature. Furthermore, cured forms of the quaternized ammonium organosilane hydrolysate displayed antimicrobial activity following 40 repeated washings.

As part of the detailed description of the invention, Rxn-2-1 & Rxn-2-2, as well as Rxn-2-1' & Rxn-2-2', depict two independent and parallel synthetic routes. To impose quaternization, the starting composition, i.e., a mixture of the two starting materials, is gradually and partially transformed via heat application. Accordingly, the "y" term in Rxn-2-2 and Rxn-2-2' denotes the mole fraction, i.e., a number from 0-1, of the components found in the resulting post-reaction composition. As can be seen, both syntheses will yield the same partially quaternized organosilane component. Other components noted in the final composition will differ among the two synthetic pathways. While the illustrations specifically depict the reaction of stoichiometric amounts of precursors, there is some flexibility in the choice of reagent ratio, as will be pointed out subsequently in the text. In the first synthetic route (Rxn-2-1), a terminally-functionalized alkyl organosilane reagent is made to react with a tertiary amine. The letter m depicts an integer from 1-6, n depicts an integer from 8-14, Z is acetoxy and/or any alkoxy group with a carbon length of 1-4, Q is X or OH, the latter being the end result of hydrolysis, and X is a leaving group terminally bonded to $(CH_2)_m$ and comprising of one or more of chlorine, bromine, iodine, and groups with a sulfonate, sulfate, phosphonate, and phosphate structure. The product of Rxn-2-1 is subsequently hydrolyzed in water according to Rxn-2-2. In the second synthetic route (Rxn-2-1'), a terminally functionalized dimethylaminoalkyl organosilane is made to react with a linear hydrocarbon bearing a primary leaving group. Again, m depicts an integer from 1-6, n is an integer from 8-14, Z is acetoxy and/or any alkoxy group with a carbon length of 1-4, Q is X or OH, the latter group being a hydrolysis product, and X is a leaving group terminally bonded to the hydrocarbon and comprising of one or more of chlorine, bromine, iodine, and groups with a sulfonate, sulfate, phosphonate, and phosphate structure.

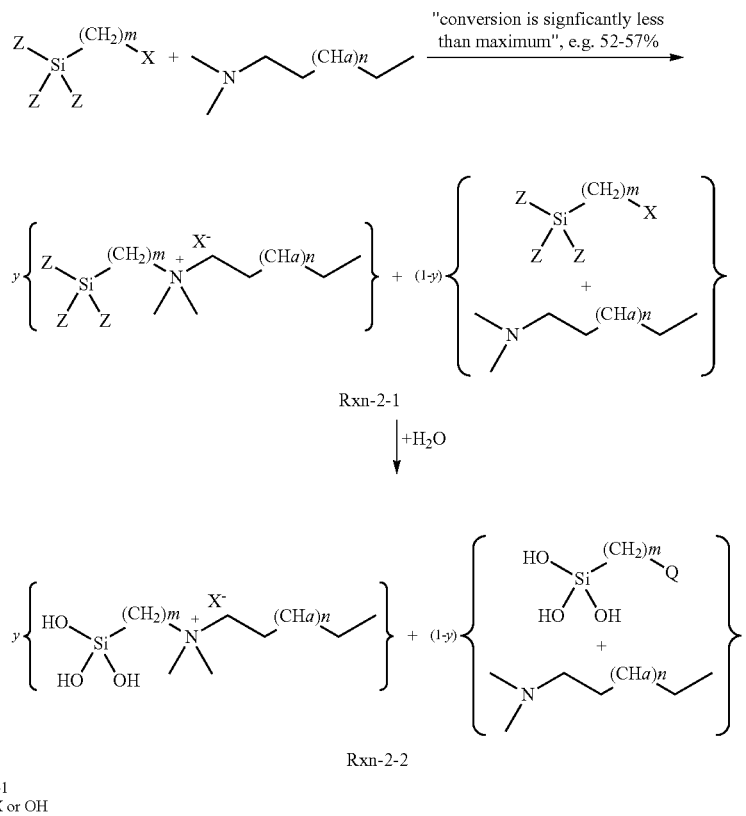

Rxn-2-1

Rxn-2-2 y = 0-1
Q = X or OH

In either parallel approach, the principle of deliberately limiting product conversion was applied, thereby attaining yields that were considerably less than that of the prior art. In either parallel approach, the same benefits were realized; the composition, once appropriately reconstituted in water, was inherently self-stabilizing at room temperature and did not precipitate out of solution. Typically, this partially quaternized composition is reconstituted in an amount of water ranging from 9- to 39-fold and preferably from 18- to 20-fold by weight, to yield a solution of quaternized hydrolysates, solvated starting materials, and hydrolyzed starting materials. Minor additional by-product components are also possible, depending on the nature of the reaction and conditions. Reiterating the original point, the hydrolysis product of commercial interest corresponds to $CH_3(CH_a)_{11-17}(CH_3)_2N^+(CH_2)_{1-6}Si(OH)_3X^-$, where "a" is 1 or 2, $(CH_2)_{1-6}$ denotes a carbon chain length between 1-6 and $CH_3(CH_a)_{11-17}$ denotes a saturated or unsaturated alkyl chain of 12-18 carbon units. That being as it may, the significant amount of solvated starting materials and their hydrolysis products (see Rxn-2-2 and Rxn-2-2') nonetheless play a decisive role in promoting the solution-phase stability of the quaternized organosilantriol end-product. Thus, all components of the post-reaction composition (i.e., the scenario after Rxn-2-2 and Rxn-2-2') bear significance in bringing out the novel features of this invention.

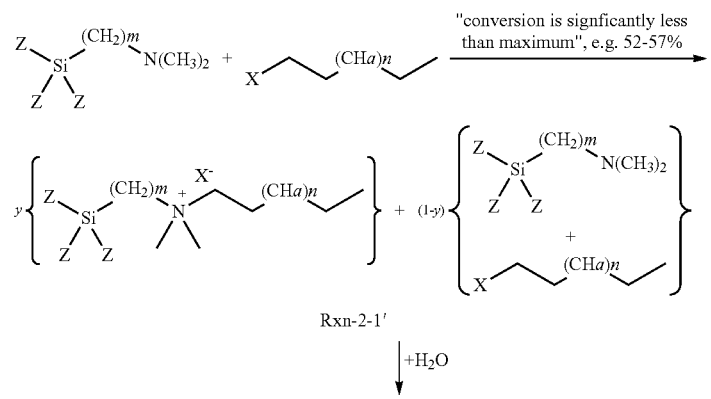

Rxn-2-1'

-continued

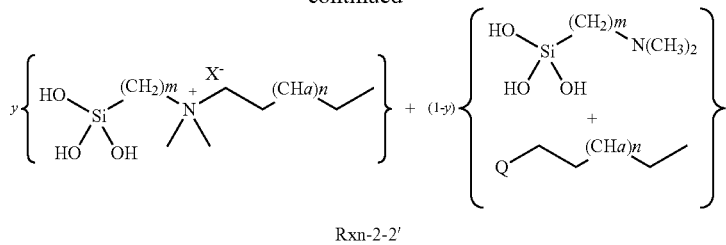

Rxn-2-2' y = 0-1
Q = X or OH

In the first step of the invention (i.e., see Rxn-2-1 and Rxn-2-1'), the partially quaternized ammonium organosilane composition was prepared by incubating the corresponding neat organosilane and tertiary amine components at elevated temperatures. The percent conversion prior to termination of the quaternization reaction—a key feature of the synthesis—was significantly less when compared to the prior art (Rxn-1 and Rxn 1'). In fact, the optimal product conversion to promote self-stabilization in water was found to vary from 52-57% when calculated on the basis of the limiting reagent. Forcing the quaternization reaction (i.e., with higher temperatures or longer reaction times) affords conversions of around 80% or higher, but the composition formed does not dissolve well and/or does not retain itself well in water. The ideal reaction temperature is approximately 115° C., however, said composition may be transformed at a temperature in the range of 85-130° C. and preferably 113-118° C. Still higher temperatures will result in thermal breakdown of the components, whereas unnecessarily low temperatures will give rise to impractically long reaction times and may facilitate the entry of atmospheric moisture. The composition must be protected from atmospheric moisture during reaction and following reaction. Reagent stoichiometry also plays a role in the quaternization reaction and the self-stabilization effect. For instance, the preferred tertiary amine-to-organosilane molar ratio was 1:1 (Rxn-2-1). Similarly, the preferred alkylchloride-to-organosilane mole/mole ratio was 1:1 (Rxn-2-1'). A molar excess of up to 50% tertiary amine (Rxn-2-1) or alkylating agent (Rxn-2-1') also produced good results. Conversely, any ratio with a significant molar excess of organosilane (e.g., greater than 15%) can yield a composition, which does not dissolve well and/or self-stabilize in water. Hence, the potentially useful molar ratio of reagents lies within the range of 0.85-1.5 (i.e., moles of tertiary amine/moles of alkylating agent).

In forming the corresponding hydrolysates as re-constituted aqueous solutions (Rxn-2-2 and Rxn-2-2'), the precipitation problem noted in the prior art was eliminated. Hence, the act of partially converting the starting materials appeared to play a key role in suppressing precipitation. It followed to reason that there would be no need to further manipulate the aqueous solutions in forming a marketable product. Looking back to the prior art (Rxn-2), additives are necessarily utilized to suppress or to delay the formation of precipitates in the aqueous medium (Rxn-2).

Hard water is to be avoided as the solvent of reconstitution, as the ions appear to have a detrimental effect on stability. Conversely, distilled water is unnecessarily pure for such an application. A grade of water that maintains adequate performance has been the deionized grade. After the reaction is cut short, the partially quaternized composition should be cooled and fed into a vat of vigorously stirred water without any unnecessary delay. As the composition readily absorbs atmospheric moisture, failure to act expediently results in crosslinking of juxtaposed components in the neat composition, yielding a water-insoluble material within a short period of exposure to air. The optimal reconstitution temperature appears to be in the range of 13-40° C. and preferably at room temperature (i.e., 24° C.). Both components, i.e., water and the quaternized composition, are combined within this temperature range. Excessive temperature during the act of dissolution spoils the product, presumably via formation of sesquioxane units and nanoscale particles. Attempts to dissolve the quaternized product under excessively cold conditions have also met with difficulties.

EXPERIMENTAL

Example 1

Synthesis of the Partially Quaternized Ammonium Organosilane Composition

Farmin DM24C brand dimethylcocoamine (11.4 g; with a typical composition of C12:49%, C14:20%, C16:11%, C18:10%) and GE A-143 brand 3-chloropropyltriethoxysilane (8.5 g) were combined in a reactor, lightly capped (or isolated from sources of humidity in the ideal case) and protected from light. With constant stirring, the temperature was ramped to 115° C. This core temperature was maintained until the percent conversion had been quantified (vide infra) and deemed optimal; in a typical case, heating from 24-28 h would afford a percentage conversion of 52-57%. Over the course of heating, a gradual discoloration of the molten composition was noted. Upon returning to room temperature, a dark-yellow, clear viscous mass was obtained.

Example 2

The % Conversion Calculation Using Sodium Tetraphenyl Borate as a Titrant

A sample (0.3-0.5 g) of the partially quaternized mass was massed and dissolved in 100 ml of distilled water. Twenty mililiters of the solution was delivered to a second vessel and diluted with another 50 ml of distilled water. Five mililiters of pH 10 buffer comprising 100 ml 0.2M $Na_2HPO_4$ and 6 ml 0.25M $Na_3PO_4$ was added. Bromophenol blue solution (12 drops) was added. With vigorous mixing, chloroform (30 ml) was added and the reaction was allowed to sit for several minutes. Once the phase separation was complete, a blue color was noted in the bottom layer. With gentler mixing, sodium tetraphenyl borate (0.01M) was added until the blue color was observed to have completely transferred to the top layer. The % conversion was estimated according to the following equation:

% Conversion=(0.5×end-point volume×[NaBPh$_4$]× apparent MW of sample)/(mass of sample in grams).

Example 3

Hydrolysis of the Partially Quaternized Ammonium Organolsilane Composition in Water, Yielding a Self-Stabilized Solution Five parts (by weight) of the partially quaternized ammonium organosilane composition prepared in Example 1 is removed from the original reactor. Without delay, this material is added to 95 parts of deionized water under rapid stirring. A solution results, which does not precipitate for 4-5 months when stored at RT and which resists freeze-thaw tests. Solutions up to 10 wt % were prepared in this manner, but their storage stability was shorter, implying an optimum concentration of 5 wt %.

Example 4

Pilot-scale Preparation of a 10 wt % Self-Stabilized Aqueous Solution of the Neat Product Farmin DM24C brand dimethylcocoamine (8.59 kg) and GE A-143 brand 3-chloropropyltriethoxysilane (6.41 kg) were sealed inside a 316 stainless steel reactor. With constant stirring, the temperature was ramped to 115° C. This core temperature was maintained until the percent conversion was identified as 53%. Still sealed, the reaction medium was allowed to cool to room temperature. The product (5 kg) was poured onto a rapidly stirring solution of deionized water (45 kg) at room temperature. Foaming and a white hazy appearance were noted initially, thereafter subsiding to yield a clear, stable solution.

Example 5

Application of the Self-stabilized Organosilantriol Solution to Textiles

The self-stabilized organosilantriol solution prepared in example 3 is diluted 20-fold in water and transferred to a tank. Textiles are dipped into the medium and later removed. The textiles are passed through rollers in order to squeeze out the excess liquid. Lastly, these organosilantriols are cured by drying the textiles in hot air (80-90° C.).

Example 6

Application of the Self-stabilized Organosilantriol Solution to Inorganic Surfaces The self-stabilized organosilantriol solution prepared in example 3 is diluted 20-fold in water. Ceramic tiles are either dip-coated in the medium or sprayed until fully wetted. The tiles are then fully dried in hot air (80-90° C.).

Example 7

Application of the Self-Stabilized Organosilantriol Solution to Organic Surfaces The self-stabilized organosilantriol solution prepared in example 3 is diluted 20-fold in water. Cardboard is sprayed until fully wetted and fully dried in hot air (80-90° C.).

Example 8

Antimicrobial Activity Findings

| Material | Colony count | Kill percentage |
| --- | --- | --- |
| Satin, unwashed | 1 | 97.4 |
| Satin, 20 washings | 6 | 84.6 |
| Cotton, unwashed | 1 | 97.8 |
| Cotton, 20 washings | 1 | 97.8 |

Washings were conducted as per standard wash-fastness tests. Bacterial growth and quantification were carried out as per standard methods. In the above table, the pathogen used was *Staphylococcus aureus*. All quantification data was referenced against native fabrics, which were similarly washed and inoculated.

Example 9

Application of the Partially Quaternized Ammonium Organosilane Composition to Compatible Liquid Precursors of Thermosetting Polymers The partially quaternized ammonium organosilane prepared in example 1 is added in the amount of 500 ppm to a stirred polyol mixture comprising polyurethane flexible foam precursors. After stirring at RT for 15 minutes, toluene diisocyanate and catalyst is added and the mixture is allowed to set.

The invention claimed is:

1. A method to synthesize an organosilyl quaternary amine composition of the type $CH_3(CH_a)_{11-17}(CH_3)_2N^+(CH_2)_{1-6}Si(Z)_3$ $X^-$ the method comprising the steps of: preparing a two-component composition, comprising: $CH_3(CH_a)_{11-17}N(CH_3)_2$ and $X(CH_2)_{1-6}Si(Z)_3$ precursor materials, combined in a $CH_3(CH_a)_{11-17}N(CH_3)_2/X(CH_2)_{1-6}Si(Z)_3$ molar ratio of 0.85-1.5; and terminating the process at a product conversion corresponding to a yield of 45 to 65%, with respect to the limiting reagent.

2. A method to synthesize an organosilyl quaternary amine composition of the type $CH_3(CH_a)_{11-17}(CH_3)_2N^+(CH_2)_{1-6}Si(Z)_3$ $X^{31}$ by preparing a two-component composition, comprising of $CH_3(CH_a)_{11-17}X$ and $(CH_3)_2N(CH_2)_{1-6}Si(Z)_3$ precursor materials, combined in a $CH_3(CH_a)_{11-17}X/(CH_3)_2N(CH_2)_{1-6}Si(Z)_3$ molar ratio of 0.85-1.5, wherein the process is terminated at a product conversion corresponding to a yield of 45 to 65%, with respect to the limiting reagent.

3. The method of claim 1 wherein said organosilyl quaternary amine composition is transformed at a temperature in the range of 85-130° C.

4. The method of claim 3 wherein said organosilyl quaternary amine composition is reconstituted using only water.

5. The method of claim 4 wherein said organosilyl quaternary amine composition is reconstituted over a temperature range of 13-40° C.

6. The method of claim 5 wherein said organosilyl quaternary amine composition is reconstituted in an amount of water ranging from 9- to 39-fold by weight, to yield an aqueous solution, which is stable at room temperature for at least two weeks.

7. The method of claim 6 wherein the thermally cured form of reconstituted solutions is antimicrobial and resistant to repeated washings.

8. The method of claim 2, wherein said organosilyl quaternary amine composition is transformed at a temperature in the range of 85-130° C.

9. The method of claim 8, wherein said organosilyl quaternary amine composition is reconstituted using only water.

10. The method of claim 9, wherein said organosilyl quaternary amine composition is reconstituted over a temperature range of 13-40° C.

11. The method of claim 10, wherein said organosilyl quaternary amine composition is reconstituted in an amount of water ranging from 9- to 39-fold by weight, to yield an aqueous solution, which is stable at room temperature for at least two weeks.

12. The method of claim 11, wherein the thermally cured form of reconstituted solutions is antimicrobial and resistant to repeated washings.

* * * * *